United States Patent
Cheetham et al.

(10) Patent No.: US 8,833,600 B2
(45) Date of Patent: Sep. 16, 2014

(54) LIQUID CONTAINER

(75) Inventors: Joshua James Cheetham, Windsor (AU); Anthony Brian Clayton, Hughesdale (AU); Amanda Jane Cosgriff, Glenhuntly (AU)

(73) Assignee: SDI North America Inc., Bensenville, IL (US)

( * ) Notice: Subject to any disclaimer, the term of this patent is extended or adjusted under 35 U.S.C. 154(b) by 0 days.

(21) Appl. No.: 13/545,039

(22) Filed: Jul. 10, 2012

(65) Prior Publication Data

US 2013/0015186 A1    Jan. 17, 2013

(30) Foreign Application Priority Data

Jul. 13, 2011   (AU) ................. 2011902790

(51) Int. Cl.
*B65D 43/04* (2006.01)
*B65D 39/16* (2006.01)
*A61C 5/06* (2006.01)

(52) U.S. Cl.
CPC ............... *A61C 5/062* (2013.01); *B65D 39/16* (2013.01)

USPC ........................... 220/801; 220/805; 215/296

(58) Field of Classification Search
USPC ............. 220/212.5, 801, 802, 804, 805, 787, 220/788, 288; 215/296, 305, 46, 50, 295; 401/118
See application file for complete search history.

(56) References Cited

U.S. PATENT DOCUMENTS

|       52,269 | A  | * |  1/1866 | Connelly ...................... 215/356 |
| 5,944,208 | A  | * |  8/1999 | Gale .............................. 215/296 |
| 7,028,858 | B2 | * |  4/2006 | Auer et al. .................... 215/318 |
|  D579,781 | S  | * | 11/2008 | Granitz .......................... D9/542 |

* cited by examiner

*Primary Examiner* — Jeffrey Allen
(74) *Attorney, Agent, or Firm* — William H. Holt

(57) ABSTRACT

A liquid container (10) has a base (12) and a cap (14) which interengage to form a hermetically sealed chamber (42). The cap (14) has a curved outer wall (18) and the base has a curved inner wall (36). The outer and inner walls (18, 36) have perspective non-circular portions and are of complementary shape. The cap (14) is able to be rotated axially relative to the base (12) by means of a handle (24) so that the outer and inner curved walls (18, 36) interact such that the cap (14) is released from the base (12) upon axial rotation thereof and the hermetic seal is broken.

9 Claims, 6 Drawing Sheets

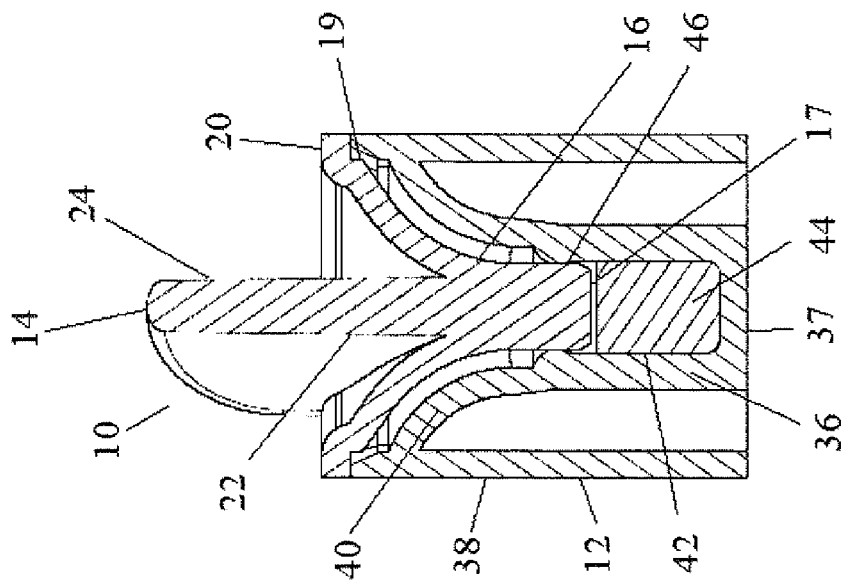
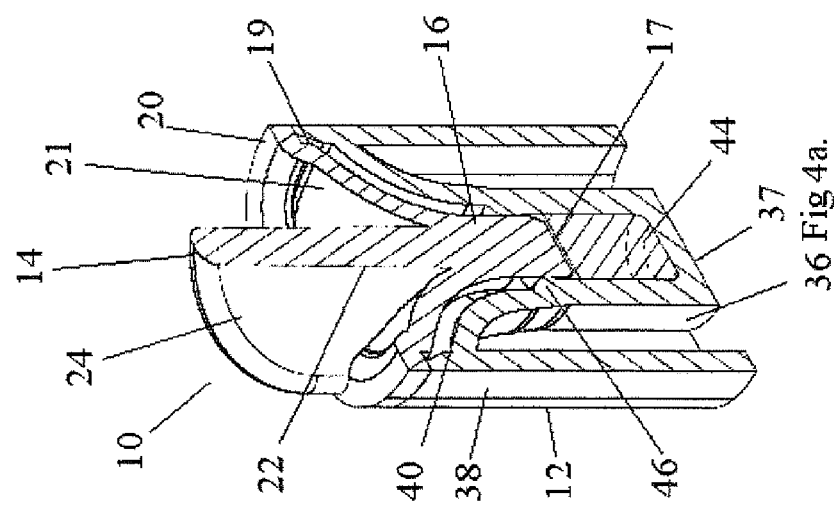

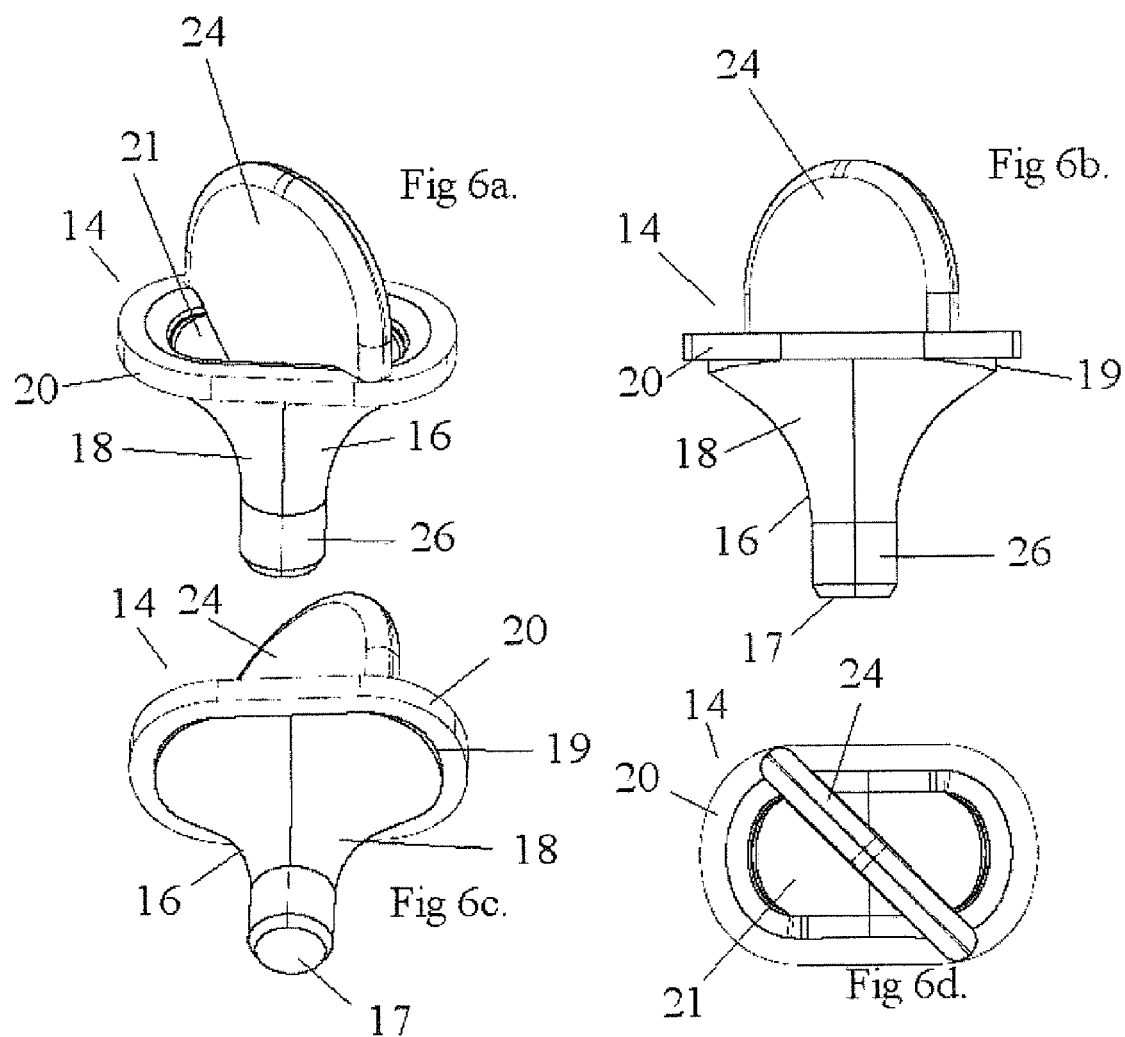

LIQUID CONTAINER

The present invention relates to a liquid container.

In accordance with one aspect of the present invention there is provided a liquid container comprising a base and a cap, the base having a lower end and an upper end and the cap having a lower end and an upper end, wherein the base and the cap are arranged to be interengaged to form a hermetic seal, such that a chamber within the base adjacent the lower end thereof is sealed off, the cap having a curved outer surface with a non-circular portion adjacent the upper end thereof and the base having a curved inner surface adjacent the upper end thereof with a non-circular portion of complementary shape to the curved non-circular portion of the outer surface of the cap, the respective upper ends being snugly engaged when the base and the cap are interengaged, the arrangement being such that the cap, when interengaged with the base, is arranged to be rotated axially so that the non-circular portion of the curved outer surface of the cap interacts with the non-circular portion of the curved inner surface of the base in such manner that the curved outer surface of the cap rises up over the upper end of the base so as to be released from the base and for the hermetic seal to be broken.

The present invention will now be described, by way of example, with reference to the accompanying drawings, in which:

FIG. 3b is an upper perspective view of the base of FIG. 3a;

FIG. 3c is a plan view of the base of FIG. 3a;

FIG. 4a is a vertical sectional view shown in perspective of and end of the container of FIGS. 1 and 2;

FIG. 4b is a view similar to FIG. 4a but is a vertical sectional front view of the container of FIGS. 1 and 2;

FIG. 6a is an upper perspective view of a cap of the container of FIGS. 1 and 2;

FIG. 6b is a side elevation of the cap shown in FIG. 6a;

FIG. 6c is an underneath perspective view of the cap shown in FIG. 6a;

FIG. 6d is a plan view of the cap shown in FIG. 6a;

In the accompanying drawings there is shown a container 10 comprising a base 12 and a cap 14.

Figure 5:
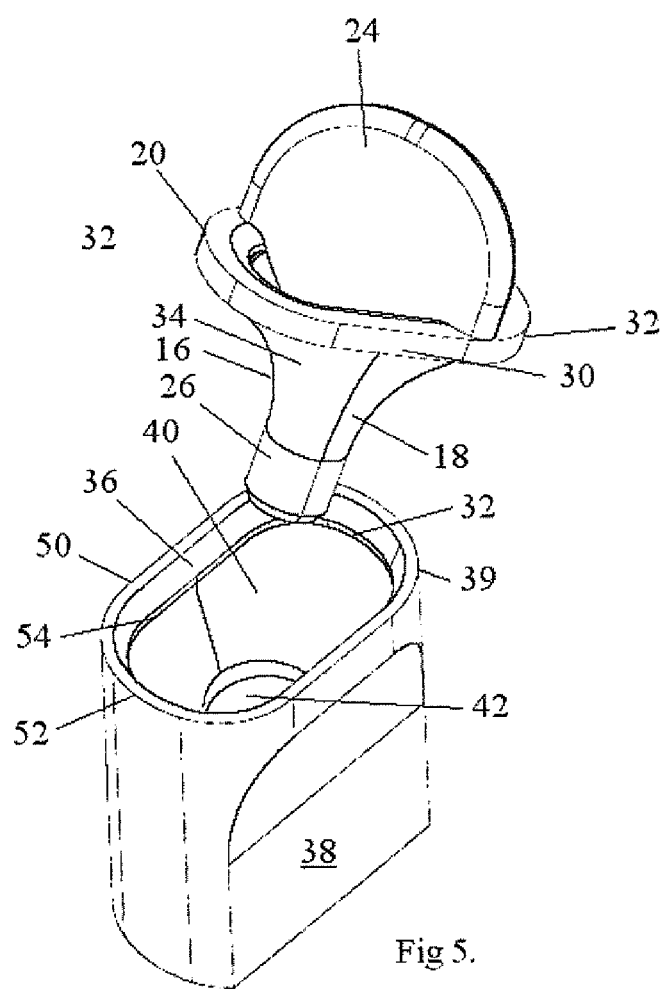
FIG. 5 is an upper perspective view of the container of FIGS. 1 and 2 in disassembled condition showing a cap being engaged with a base.

As can be seen in FIGS. 4 to 6, it can be seen that the cap 14 comprises an elongated body 16. The body 16 has a first lower end 17 and a second upper end 19. An outer wall 18 extends from the first end 17 to the second end 19 of the body 16.

An endless rim 20 extends outwardly from the second end 19 and surrounds the upper end 19 of the cap 14.

A flange 22 extends upwardly from the body 16 and extends into a handle 24. The handle 24 is arranged to be rotated manually to cause the cap 14 to rotate axially in use.

The body 16 has a lower portion 26 which is generally circular in outer shape. Further the rim 20 has flat sides 30 and curved ends 32. The outer wall 18 is generally circular adjacent the lower portion 26 but as shown flares outwardly progressively towards the rim 20. Further, adjacent the rim 20, the outer wall 18 has a shape similar to that of the rim 20 as shown in FIG. 6c.

The base 12 has an inner wall 36 which is generally circular adjacent a lower end 37 thereof. The wall 36 is connected to outer sides 38 of the base 12 adjacent an upper end of the wall 36 by means of an outwardly extending circumferential flange 40. The flange 40 acts as a guide for insertion of the cap 14 as will be described. Further, the flange 40 adopts a shape corresponding to that of the base 12 adjacent an upper end 39 thereof.

The wall 36 defines a liquid chamber 42 of the container 10 as can be seen by liquid 44 shown in FIGS. 4a and 4b. Further, the bottom of the liquid chamber 42 could have a tapered or conical shape in place of the flat bottom shown in FIGS. 4a and 4b.

Further, the chamber 42 is provided adjacent an upper end thereof with a circumferential inwardly extending projection 46 as shown in FIGS. 4a and 4b which is arranged to engage the lower cylindrical end 26 of the cap 14 sealingly to form a hermetic seal.

Figure 3A:
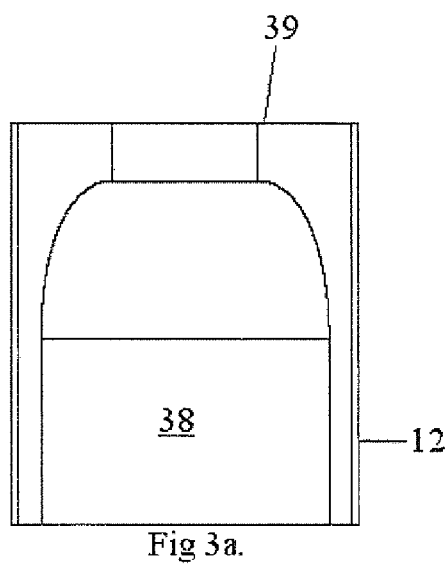
FIG. 3a is a side elevation of a base of the container of FIGS. 1 and 2.
Figure 3B:
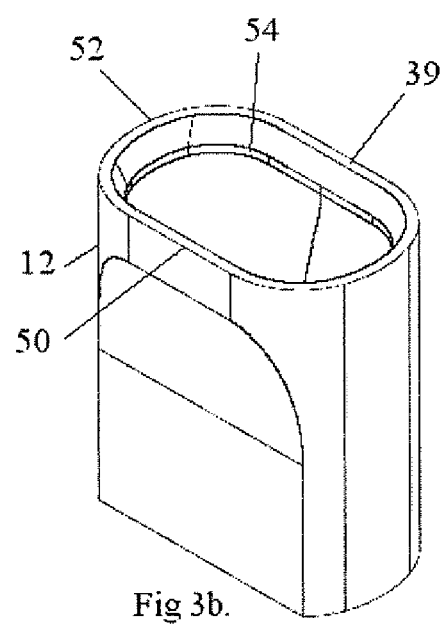
Figure 3C:
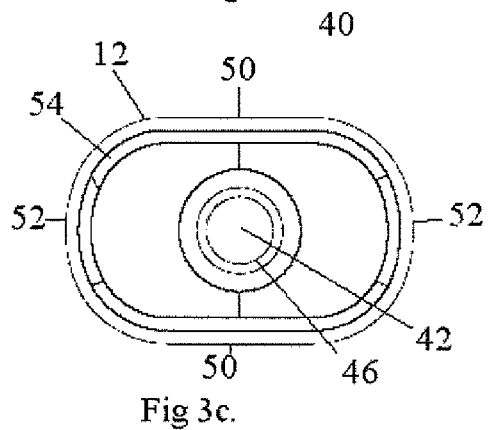

As can be seen in FIGS. 3b and 3c, the upper end 39 of the base 12 has flat sides 50 interconnected by curved ends 52 to correspond with the shape of the rim 20 described hereinabove. Further a lip 54 of similar shape is disposed within the base 12.

In use, the cap 14 is pushed into the base 12 guided by the flange 40 until the lower end 26 of the body 16 engages with the projection 46 and the rim 20 engages with the end 19 as shown in FIGS. 4a and 4b. The liquid chamber 42 is, in this condition, hermetically sealed.

This protects the liquid 44 contents of the chamber 42 from the atmosphere and, if the container 10 is opaque, also from the ambient light.

Figure 1:
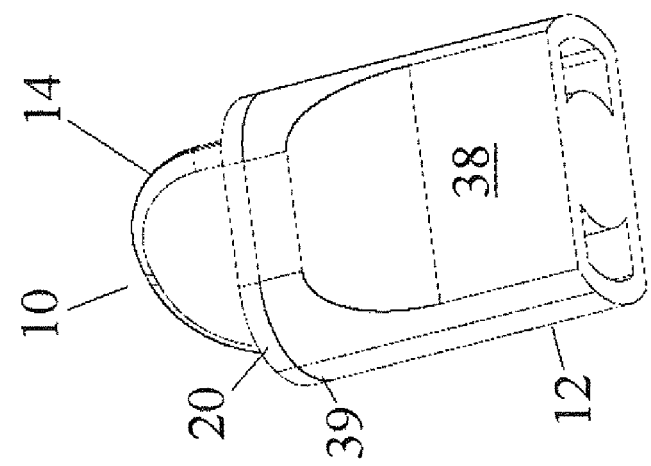
FIG. 1 is an upper perspective front view of a container in accordance with the present invention.
Figure 2:
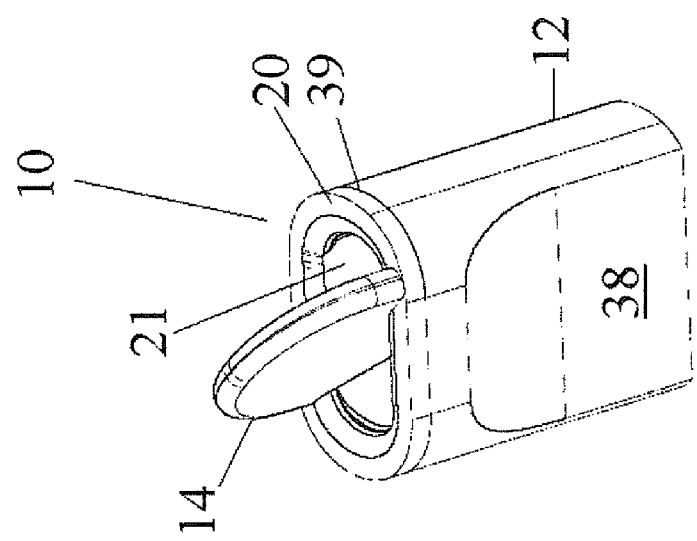
FIG. 2 is an underneath perspective front view of the container of FIG. 1.
Figure 7A:
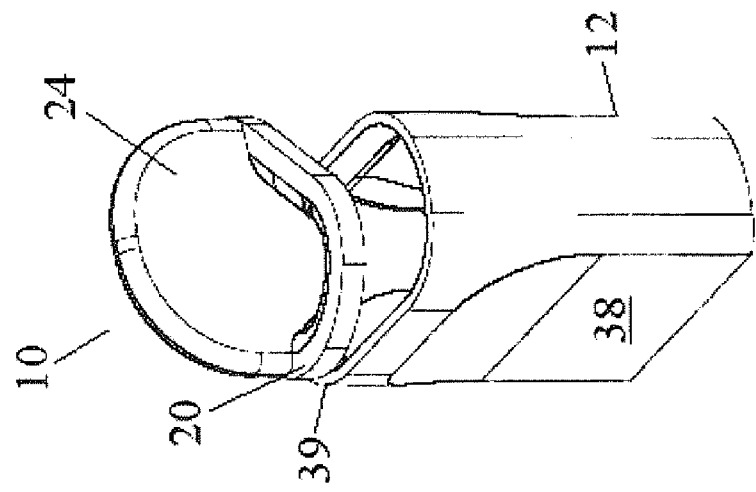
FIG. 7a is an upper perspective side view of the container of FIGS. 1 and 2.
Figure 7B:
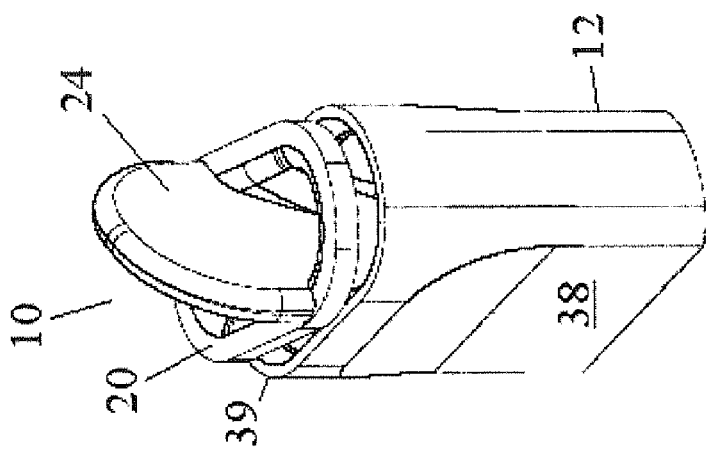
FIG. 7b is a view similar to FIG. 7a showing a cap being rotated and removed from a base.
Figure 7C:
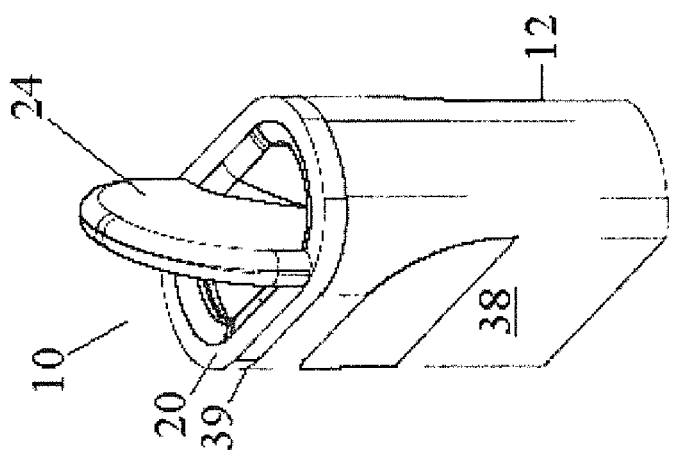
FIG. 7c is a view similar to FIG. 7b showing the cap rotated further and being further removed from the base.

In the condition shown in FIGS. 1 and 2, the engaged cap 14 is arranged to be manually rotated clockwise or anticlockwise by means of the handle 24 so that the shaped upper end 19 of the body 16 of the cap 14 interacts with the shaped inner upper end 39 of the base 12. As relative rotation of the cap 14 and the base 12 is continued the body 16 is caused to rise up over the inner upper end 39 of the wall 36 of the base 12 causing the cap 14 to be moved out of the base 12 and the hermetic seal to be broken. This sequence is shown in FIGS. 7a to 7c. In FIG. 7a the cap 14 is engaged with the base 12. In FIG. 7b the cap 14 is partially rotated and is partially disengaged from the base 12. Finally, in FIG. 7c the cap 14 is further rotated and disengaged from the base 12 and is about to be removed entirely therefrom as shown in FIG. 5.

It is envisaged that the liquid container 10 of the present invention be of general applicability but it is particularly envisaged to be used with dental adhesives or liquid dental cements.

Modifications and variations as would be apparent to a skilled addressee are deemed to be within the scope of the present invention. For example, optionally an inner base of the upper end 39 of the wall 36 could be radiused although this is not essential.

The invention claimed is:

1. A liquid container comprising a base and a cap, wherein said base has a lower end and an upper end and said cap has a lower end and an upper end, said cap having an outer wall extending from its lower end to its upper end thereof, said base having outer sides and an inner wall connected to said outer sides adjacent an upper end of said inner wall, and wherein said base and said cap are arranged to be interengaged for forming an hermetic seal wherein a chamber located within said base adjacent said lower end thereof is sealed off, said outer wall of said cap having a circular outer surface adjacent said lower end thereof and said outer wall of said cap having a non-circular outer surface adjacent said upper end thereof in which said non-circular outer surface has opposed curved lateral end portions interconnected by side walls, said inner wall of said base having a non-circular inner surface adjacent an upper end thereof in which said non-circular inner surface has opposed curved lateral end portions connected by side walls and being of complementary shape to said upper portion of said outer wall of said cap, the respective upper ends being snugly engaged when said base and said cap are interengaged, the arrangement being such that said cap, when interengaged with said base, is arranged to be rotated axially so that said upper end portion of said outer wall of said cap intersects with said upper end of said inner wall of said base in such manner that said upper end of said wall of said cap rises up over said upper end of said inner wall of said base so as to be released from said base and for said hermetic seal to be broken.

2. A liquid container according to claim 1 wherein said lower end of said cap is arranged for engaging sealingly with said chamber for forming said hermetic seal, said lower end of said engaged cap being spaced from said lower end of said base for defining said hermetically sealed chamber.

3. A liquid container according to claim 1 wherein said cap has a handle for enabling said cap to be rotated axially relative to said base.

4. A liquid container according to claim 1 wherein said cap has an outwardly extending rim arranged for engaging with said upper end of said base when said chamber is hermetically sealed.

5. A liquid container according to claim 1 wherein said base comprises a generally circular inner wall adjacent said lower end thereof, which inner wall defines said chamber.

6. A liquid container according to claim 1 wherein an upper region of said outer wall of said cap is flared progressively outwardly towards said upper end of said cap.

7. A liquid container according to claim 1 wherein said non-circular outer surface of said outer wall of said cap has a pair of opposed generally flat side walls interconnecting said opposed curved lateral end portion of said cap.

8. A liquid container according to claim 1 wherein said non-circular inner surface of said inner wall of said base has a pair of opposed generally flat side walls interconnecting said opposed curved lateral end portions of said inner wall.

9. A liquid container according to claim 1 wherein said chamber contains a liquid.

\* \* \* \* \*